United States Patent [19]

Sum et al.

[11] Patent Number: 5,284,963
[45] Date of Patent: Feb. 8, 1994

[54] METHOD OF PRODUCING 7-(SUBSTITUTED)-9-[(SUBSTITUTED GLYCYL)-AMIDOL]-6-DEMETHYL-6-DEOX-YTETRA-CYCLINES

[75] Inventors: Phaik-Eng Sum, Pomona; Ving J. Lee, Monsey, both of N.Y.

[73] Assignee: American Cyanamid Company, Wayne, N.J.

[21] Appl. No.: 928,588

[22] Filed: Aug. 13, 1992

[51] Int. Cl.$^5$ .................. C07C 233/64; C07C 235/32
[52] U.S. Cl. .................. 552/205; 540/200; 544/154; 546/195; 548/263.2; 548/267.6; 548/538; 548/316.4; 548/300.4
[58] Field of Search .................. 552/205; 540/200; 544/154; 546/195; 548/263.2, 267.6, 357, 356, 538

[56] References Cited

U.S. PATENT DOCUMENTS

| | | | |
|---|---|---|---|
| Re. 26,253 | 8/1967 | Petisi | 260/559 |
| Re. 26,271 | 9/1967 | Boothe | 260/559 |
| 2,482,055 | 9/1949 | Duggar . | |
| 3,007,965 | 11/1961 | Growich . | |
| 3,043,875 | 7/1962 | Beereboom . | |
| 3,200,149 | 8/1965 | Blackwood . | |
| 3,226,436 | 12/1965 | Petisi . | |
| 3,338,963 | 8/1967 | Petisi . | |
| 3,341,585 | 9/1967 | Bitha . | |
| 3,360,557 | 12/1967 | Shu . | |
| 3,360,561 | 12/1967 | Zambrano . | |
| 3,518,306 | 6/1970 | Martell . | |
| 5,021,407 | 6/1991 | Levy | 514/154 |

OTHER PUBLICATIONS

Chopra, Handbook of Experimental Parmacology, vol. 78, 317–392, Springer-Verlag (1985).
Levy, Antimicrobial Agents and Chemotherapy, vol. 33, No. 8, 1373–1374, (Aug. 1989).
Salyers, Molecular Microbiology, 4(1), 151–156 (1990).

*Primary Examiner*—Howard T. Mars
*Assistant Examiner*—Kimberly J. Kestler
*Attorney, Agent, or Firm*—T. S. Szatkowski

[57] ABSTRACT

The invention provides a novel method for producing compounds of the formula I:

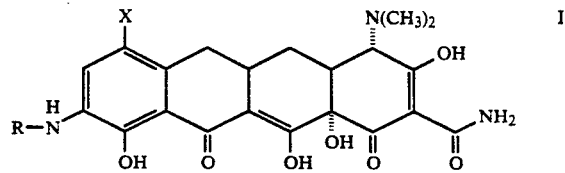

wherein X and R are defined in the specifications. The invention also provides a method for making intermediates useful to produce the compounds of formula I. Utilizing a common intermediate, the novel method efficiently produces compounds of the formula I.

11 Claims, No Drawings

METHOD OF PRODUCING 7-(SUBSTITUTED)-9-[(SUBSTITUTED GLYCYL)-AMIDOL]-6-DEMETHYL-6-DEOXYTETRA-CYCLINES

BACKGROUND OF THE INVENTION

Field of the Invention

The invention relates to a novel method for producing [4S-(4alpha,12aalpha)]-4-(dimethylamino)-7-(substituted)-9-[[(substituted amino)substituted]amino]-1,4,4a,5,5a,6,11,12a-octahydro-3,10,12,12a-tetrahydroxy-1,11-dioxo-2-naphthacenecarboxamides, hereinafter called 7-(substituted)-9-[(substituted glycyl)amido]-6-demethyl-6-deoxytetracyclines, which are useful as antibiotic agents.

The invention also relates to making novel, straight or branched 9-[(haloacyl)amido]-7-(substituted)-6-demethyl-6-deoxytetracycline intermediates, which are useful for making the novel compounds of the present invention.

SUMMARY OF THE INVENTION

This invention is concerned with a novel method for producing 7-(substituted)-9-[(substituted glycyl)amido]-6-demethyl-6-deoxytetracyclines, represented by formula I:

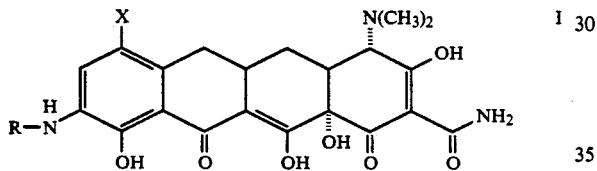

wherein:
X is selected from amino, —NR$^1$R$^2$, or halogen; the halogen is selected from bromine, chlorine, fluorine and iodine;
and when X= and R$^1$=hydrogen, R$^2$=methyl, ethyl, n-propyl, 1-methylethyl, n-butyl, 1-methylpropyl, 2-methylpropyl or 1,1-dimethylethyl;
and when R$^1$=methyl or ethyl, R$^2$=methyl, ethyl, n-propyl, 1-methylethyl, n-butyl, 1-methylpropyl or 2-methylpropyl;
and when R$^1$=n-propyl, R$^2$=n-propyl, 1-methylethyl, n-butyl, 1-methylpropyl or 2-methylpropyl;
and when R$^1$=1-methylethyl, R$^2$=n-butyl, 1-methylpropyl or 2-methylpropyl;
and when R$^1$=n-butyl, R$^2$=n-butyl, 1-methylpropyl or 2-methylpropyl;
and when R$^1$=1-methylpropyl, R$^2$=2-methylpropyl;
R is selected from R$^4$(CH$_2$)$_n$CO, n=0–4, and when n=0, R$^4$ is selected from γ-amino(C$_1$–C$_4$)alkyl group [selected from α-aminomethyl, α-aminoethyl, α-aminopropyl, α-aminobutyl and the enantiomers of said α-amino(C$_1$–C$_4$)alkyl group]; α-aralkylamino group [selected from phenylglycyl and the enantiomers of said α-aralkylamino group];
and when n=1–4, R$^4$ is selected from amino; monosubstituted amino group [selected from straight or branched (C$_1$–C$_6$)alkyl (substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethybutyl and 1-methyl-2-ethylpropyl), cyclopropylamino, cyclobutylamino, benzylamino and phenylamino]; disubstituted amino group [selected from dimethylamino, diethylamino, methyl(butyl)amino, ethyl(1-methylethyl)amino, monomethylbenzylamino, aziridinyl, azetidinyl, pyrrolidinyl, 2-methylpyrrolidinyl, piperidinyl, morpholinyl, imidazolyl, 1-pyrrolyl, 1-(1,2,3-triazolyl) and 4-(1,2,4-triazolyl)]; carboxy(C$_2$–C$_4$)alkylamino group [selected from aminoacetic acid, α-aminopropionic acid and the enantiomers of said carboxy(C$_2$–C$_4$)alkylamino group]; which method comprises reacting a haloacyl halide compound of the formula:

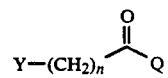

wherein when n=0, Y is straight or branched α-halo (C$_1$–C$_4$)alkyl group [selected from bromomethyl, chloromethyl, iodomethyl, α-bromoethyl, α-chloroethyl, α-bromobutyl and α-chloro-isobutyl];
and when n=1–4, Y is halogen [selected from bromine, chlorine, iodine and fluorine], O-toluenesulfonate, O-methylsulfonate or trifluoromethylsulfonate;
and Q is halogen [selected from bromine, chlorine, fluorine and iodine] with a 9-amino-7-(substituted)-6-demethyl-6-deoxytetracycline compound of the formula:

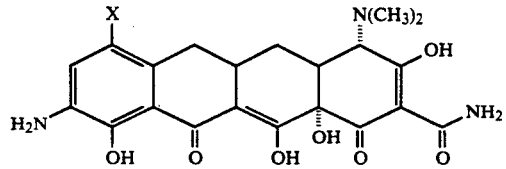

wherein X is as defined hereinabove or the pharmacologically acceptable organic and inorganic salts thereof to obtain a 9-[(haloacyl)amido]-7-(substituted)-6-demethyl-6-deoxytetracycline intermediate of the formula:

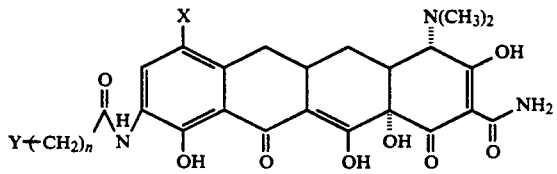

wherein X, Y and n are as defined hereinabove or the organic or inorganic salts thereof and reacting the intermediate, 9-[(haloacyl)amido]-7-(substituted)-6-demethyl-6-deoxytetracycline or the pharmacologically acceptable organic and inorganic salts thereof, with a nucleophile of the formula R$^4$H, wherein R$^4$ is as defined hereinabove, to obtain a 7-(substituted)-9-[(substituted glycyl)amido]-6-demethyl-6-deoxytetracycline compound according to formula I or the organic and inorganic salts thereof.

This novel method is an efficient way of preparing the 7-(substituted)-9-[(substituted glycyl)amido]-6-demethyl-6-deoxytetracycline or the pharmacologically acceptable organic and inorganic salts. The novel method permits these compounds to be prepared in two reactions. The first reaction results in the formation of a common intermediate, 9-[(haloacyl)amido]-7-(substituted)-6-demethyl-6-deoxytetracycline or the pharmacologically acceptable organic and inorganic salts thereof. The second reaction permits the common intermediate to be reacted with a wide variety of amines and results in a wide spectrum of 7-(substituted)-9-[(substituted glycyl)amido]-6-demethyl-6-deoxytetracyclines or the pharmacologically acceptable organic and inorganic salts thereof. The use of difficult protecting groups is eliminated, thus allowing the final products to be formed in only two reactions.

Preferred is a method for producing compounds according to the above formula I wherein:

X is selected from amino, —NR$^1$or halogen; the halogen is selected from bromine, chlorine, fluorine and iodine;

and when X=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl;

and when R$^1$=methyl or ethyl, R$^2$=methyl, ethyl, n-propyl, 1-methylethyl, n-butyl; R is selected from R$^4$(CH$_2$)$_n$CO, n=0-4, and when n=0, R$^4$ is selected from α-amino(C$_1$-C$_4$)alkyl group [selected from α-aminomethyl, α-aminoethyl, α-aminopropyl, α-aminobutyl and the enantiomers of said α-amino(C$_1$-C$_4$)alkyl group]; α-aralkylamino group [selected from phenylglycyl and the enantiomers of said α-aralkylamino group]; and when n=1-4, R$^4$ is selected from amino; monosubstituted amino group [selected from straight or branched (C$_1$-C$_6$)alkyl (substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethybutyl and 1-methyl-2-ethylpropyl), cyclopropylamino, cyclobutylamino, benzylamino and phenylamino]; disubstituted amino group [selected from dimethylamino, diethylamino, methyl(butyl)amino, ethyl(1-methylethyl)amino, monomethylbenzylamino, aziridinyl, azetidinyl, pyrrolidinyl, 2-methylpyrrolidinyl, piperidinyl, morpholinyl, imidazolyl, 1-pyrrolyl, 1-(1,2,3-triazolyl) and 4-(1,2,4-triazolyl)]; carboxy(C$_2$-C$_4$)alkylamino group [selected from aminoacetic acid, α-aminopropionic acid and the enantiomers of said carboxy(C$_2$-C$_4$)alkylamino group]; and the pharmacologically acceptable organic and inorganic salts.

Particularly preferred is a method for producing compounds according to formula I wherein: X is selected from amino, —NR$^1$R$^2$, or halogen; the halogen is selected from bromine, chlorine, fluorine and iodine;

and when X= and R$^1$=hydrogen, R$^2$=methyl, ethyl, n-propyl, 1-methylethyl, n-butyl, 1-methylpropyl, 2-methylpropyl or 1,1-dimethylethyl;

and when R=methyl or ethyl, R$^2$=methyl, ethyl, n-propyl, 1-methylethyl, n-butyl, 1-methylpropyl or 2-methylpropyl;

R is selected from R$^4$(CH$_2$)$_n$CO, , n=0-4, and when n=0, R$^4$ is selected from α-amino(C$_1$-C$_4$)alkyl group [selected from α-aminomethyl, α-aminoethyl, α-aminopropyl, α-aminobutyl and the enantiomers of said α-amino(C$_1$-C$_4$)alkyl group]; α-aralkylamino group [selected from phenylglycyl and the enantiomers of said α-aralkylamino group];

and when n=1-4, R$^4$ is selected from amino; monosubstituted amino group [selected from straight or branched (C$_1$-C$_6$)alkyl (substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethybutyl and 1-methyl-2-ethylpropyl), cyclopropylamino, cyclobutylamino and benzylamino]; disubstituted amino group [selected from dimethylamino, diethylamino, methyl(butyl)amino, ethyl(1-methylethyl)amino, monomethylbenzylamino, aziridinyl, azetidinyl, pyrrolidinyl, 2-methylpyrrolidinyl, piperidinyl, morpholinyl, imidazolyl, 1-pyrrolyl, 1-(1,2,3-triazolyl) and 4-(1,2,4-triazolyl)]; carboxy(C$_2$-C$_4$)alkylamino group [selected from aminoacetic acid, α-aminopropionic acid and the enantiomers of said carboxy(C$_2$-C$_4$)alkylamino group]; and the pharmacologically acceptable organic and inorganic salts.

Most particularly preferred is a method for producing compounds according to formula I wherein:

X is selected from amino, —NR$^1$R$^2$, or halogen; the halogen is selected from bromine, chlorine, fluorine and iodine;

and when X=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl; and when R$^1$=methyl or ethyl, R$^2$=methyl, ethyl, n-propyl, 1-methylethyl, n-butyl, 1-methylpropyl or 2-methylpropyl;

R is selected from R$^4$(CH$_2$)$_n$CO, n=0-4, and when n=0, R$^4$ is selected from α-amino(C$_1$-C$_4$)alkyl group [selected from α-aminomethyl, α-aminoethyl, α-aminopropyl, α-aminobutyl and the enantiomers of said α-amino(C$_1$-C$_4$)alkyl group];

and when n=1-4, R$^4$ is selected from amino; monosubstituted amino group [selected from straight or branched (C$_1$-C$_6$)alkyl (substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethybutyl and 1-methyl-2-ethylpropyl), cyclopropylamino, cyclobutylamino and benzylamino]; disubstituted amino group [selected from dimethylamino, diethylamino, methyl(butyl)amino, ethyl(1-methylethyl)amino, monomethylbenzylamino, aziridinyl, azetidinyl, pyrrolidinyl, 2-methylpyrrolidinyl, piperidinyl, morpholinyl, imidazolyl and 1-pyrrolyl]; carboxy(C$_2$-C$_4$)alkylamino group [selected from aminoacetic acid]; and the pharmacologically acceptable organic and inorganic salts.

Of special interest is a method for producing compounds according to formula I wherein: X is selected from amino, —NR$^1$R$^2$, or halogen; the halogen is selected from bromine, chlorine, fluorine and iodine;

and when X=—NR$^1$R$^2$ and when R$^1$=methyl or ethyl, R$^2$=methyl or ethyl;

R is selected from R$^4$(CH$_2$)$_n$CO, n=0–4, and when n=0, R$^4$ is selected from α-amino(C$_1$–C$_4$)alkyl group [selected from α-aminomethyl, α-aminoethyl, and the enantiomers of said α-amino(C$_1$–C$_4$)alkyl group];

and when n=1–4, R$^4$ is selected from amino; monosubstituted amino group [selected from straight or branched (C$_1$–C$_6$)alkyl (substitution selected from methyl, ethyl, n-propyl, 1-methylethyl, n-butyl, n-pentyl and n-hexyl), cyclopropylamino and benzylamino]; disubstituted amino group [selected from dimethylamino, diethylamino, methyl(butyl)amino, azetidinyl, pyrrolidinyl, piperidinyl, morpholinyl and 1-imidazolyl];

and the pharmacologically acceptable organic and inorganic salts.

Also included in the present invention is a method for making a novel straight or branched 9-[(haloacyl)amido]-7-(substituted)-6-demethyl-6-deoxytetracycline intermediate useful for producing the above compounds of formula I. Such intermediate includes those having the formula II:

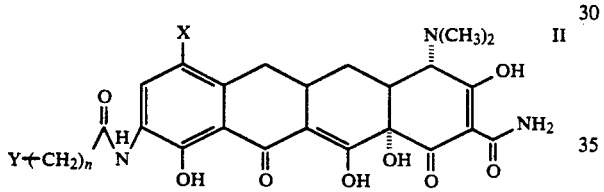

wherein:

X is selected from amino, —NR$^1$R$^2$, or halogen; the halogen is selected from bromine, chlorine, fluorine and iodine;

and when X=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl;

and when R$^1$=methyl or ethyl, R$^2$=methyl, ethyl, n-propyl, 1-methylethyl, n-butyl, 1-methylpropyl or 2-methylpropyl;

and when R$^1$=n-propyl, R$^2$=n-propyl, 1-methylethyl, n-butyl, 1-methylpropyl or 2-methylpropyl;

and when R$^1$=1-methylethyl, R$^2$=n-butyl, 1-methylpropyl or 2-methylpropyl;

and when R$^1$=n-butyl, R$^2$=n-butyl, 1-methylpropyl or 2-methylpropyl;

and when R$^1$=1-methylpropyl, R$^2$=2-methylpropyl;

and when n=0, Y is straight or branched α-halo(C$_1$–C$_4$)alkyl group [selected from bromomethyl, chloromethyl, iodomethyl, α-bromoethyl, α-chloroethyl, α-bromobutyl and α-chloro-isobutyl];

and when n=1–4, Y is halogen [selected from bromine, chlorine, iodine and fluorine], O-toluenesulfonate, O-methylsulfonate or trifluoromethylsulfonate; and the pharmacologically acceptable organic and inorganic salt.

The novel method for producing the intermediate compound of formula II comprises reacting a 9-amino-7-(substituted)-6-demethyl-6-deoxytetracycline with a compound of the formula:

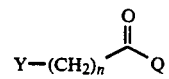

wherein Y, n and Q are as defined hereinabove.

Preferred is a method for producing compounds according to the above formula II wherein:

X is selected from amino, —NR$^1$R$^2$, or halogen; the halogen is selected from bromine, chlorine, fluorine and iodine;

and when X=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl; and when R$^1$=methyl or ethyl, R$^2$=methyl, ethyl, n-propyl, 1-methylethyl, n-butyl;

and when n=0, Y is straight or branched α-halo(C$_1$<–C$_4$)alkyl group [selected from bromomethyl, chloromethyl, iodomethyl, α-bromoethyl, α-chloroethyl, α-bromobutyl and α-chloro-isobutyl];

and when n=1–4, Y is halogen [selected from bromine, chlorine, iodine and fluorine], O-toluenesulfonate, O-methylsulfonate or trifluoromethylsulfonate; and the pharmacologically acceptable organic and inorganic salt.

Particularly preferred is a method for producing compounds according to formula II wherein:

X is selected from amino, —NR$^1$R$^2$, or halogen; the halogen is selected from bromine, chlorine, fluorine and iodine;

and when X=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl; and when R$^1$=methyl or ethyl, R$^2$=methyl, ethyl, n-propyl, 1-methylethyl, n-butyl, 1-methylpropyl or 2-methylpropyl;

and when n=0, Y is straight or branched α-halo(C$_1$–C$_4$)alkyl group [selected from bromomethyl, chloromethyl, iodomethyl, α-bromoethyl, α-chloroethyl, α-bromobutyl and α-chloro-isobutyl];

and when n=1–4, Y is halogen [selected from bromine, chlorine, iodine and fluorine], O-toluenesulfonate, O-methylsulfonate or trifluoromethylsulfonate; and the pharmacologically acceptable organic and inorganic salt.

Most particularly preferred is a method for producing compounds according to formula II wherein:

X is selected from amino, —NR$^1$R$^2$, or halogen; the halogen is selected from bromine, chlorine, fluorine and iodine;

and when X=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl;

and when R$^1$=methyl or ethyl, R$^2$=methyl, ethyl, n-propyl, 1-methylethyl, n-butyl, 1-methylpropyl or 2-methylpropyl;

and when n=0, Y is straight or branched α-halo(C$_1$–C$_4$)alkyl group [selected from bromomethyl, chloromethyl, iodomethyl, α-bromoethyl, α-chloroethyl, α-bromobutyl and α-chloro-isobutyl];

and when n=1–4, Y is halogen [selected from bromine, chlorine, iodine and fluorine], O-toluenesulfonate, O-methylsulfonate or trifluoromethylsulfonate; and the pharmacologically acceptable organic and inorganic salt.

Of special interest is a method for producing compounds according to formula II wherein:

X is selected from amino, —NR$^1$R$^2$, or halogen; the halogen is selected from bromine, chlorine, fluorine and iodine;

and when X=—NR$^1$R$^2$ and when R$^1$=methyl or ethyl, R$^2$=methyl or ethyl; and when n=0, Y is straight or branched α-halo(C$_1$-C$_4$)alkyl group [selected from bromomethyl, chloromethyl, iodomethyl, α-bromoethyl, α-chloroethyl, α-bromobutyl and α-chloro-isobutyl];

and when n=1-4, Y is halogen [selected from bromine, chlorine, iodine and fluorine], O-toluenesulfonate, O-methylsulfonate or trifluoromethylsulfonate; and the pharmacologically acceptable organic and inorganic salt.

DESCRIPTION OF THE PREFERRED EMBODIMENTS

The novel method of the present invention, Scheme III, provides an easier way of preparing 7-(substituted)-9-[(substituted glycyl)amido]-6-demethyl-6-deoxytetracyclines or their pharmacologically acceptable organic and inorganic salts. This novel method provides a way to prepare some of the 7-(substituted)- 9-[(substituted glycyl)amido]-6-demethyl-6-deoxytetracyclines or their pharmacologically acceptable organic and inorganic salts that would be very difficult to prepare using either of the prior art methods shown in Scheme I or II.

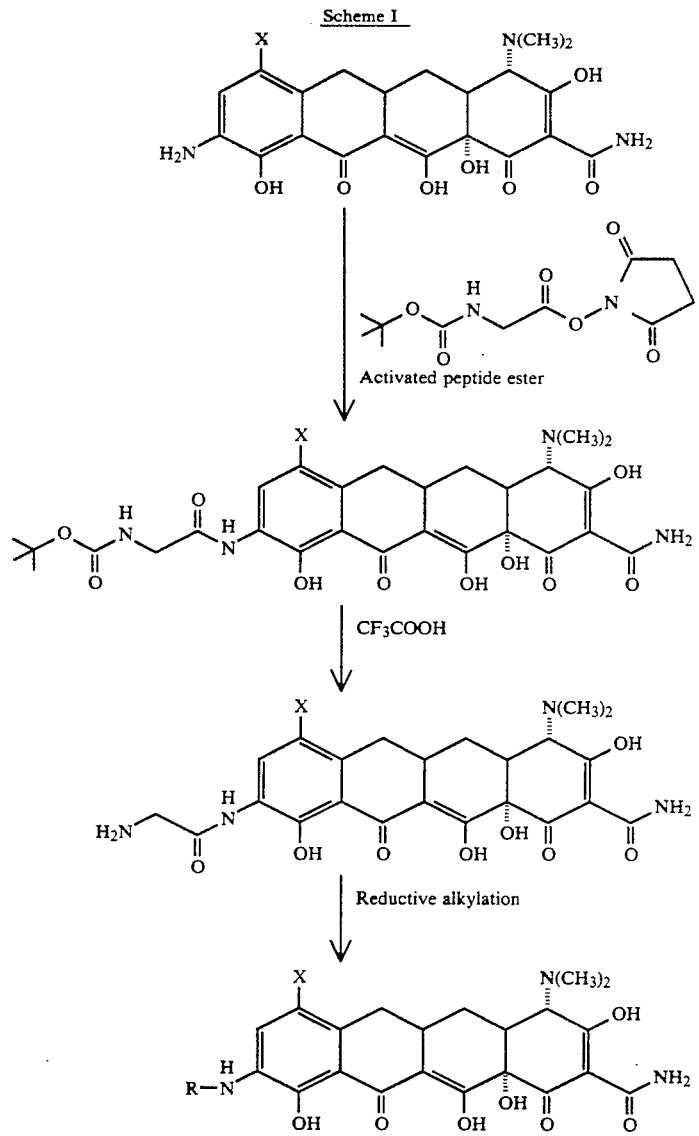

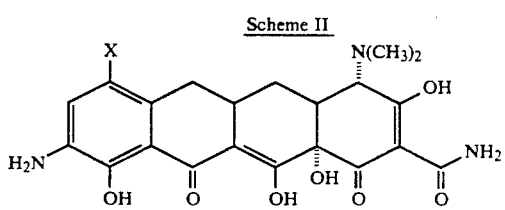

-continued
Scheme II

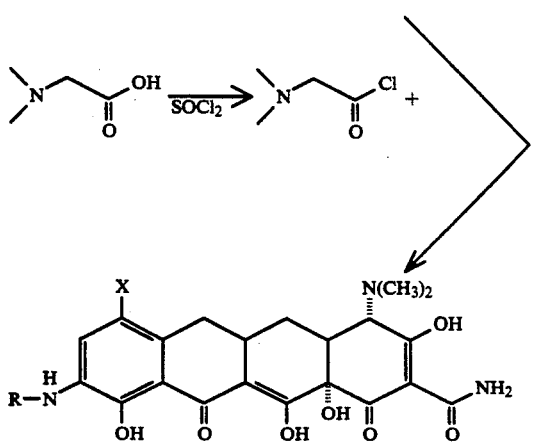

The method shown in Scheme I is premised on a reductive N-alkylation of the 9-(glycylamido)-7-(substituted)-6-demethyl-6-deoxytetracycline. It is possible to use this method only when two identical substituents are incorporated on the nitrogen. It would be unworkable to incorporate sequentially two different substituents on the nitrogen because the reductive alkylation conditions are such that both hydrogens are substituted at the same time. Thus, using the method of Scheme I, it would not be possible to incorporate a single substituent efficiently. In addition, the initial reaction of the (succinyloxycarbonyl)methyl carbamic acid tert-butyl ester with the appropriate 9-amino-7-(substituted)-6-demethyl-6-deoxytetracycline affords only moderate yields.

The method shown in Scheme II is premised on forming an acid chloride from a mono- or disubstituted ($C_1$-$C_6$)amino substituted acyl acid and reacting the so formed acid chloride with the amine at the 9-position of the 9-amino-7-(substituted)-6-demethyl-6-deoxytetracycline. Typically, the acid chloride is formed by the reaction of the appropriate mono- or disubstituted($C_1$-$C_6$)amine with either haloacetic acids (or esters) or their synthetic equivalents, e.g., p-toluenesulfonyloxyacetic acid or methanesulfonyloxyacetic acid. In the case of N-(monosubstituted)amino acids, the method shown in Scheme II may be utilized only via the use of nitrogen protecting groups. However, the protecting groups must survive the acyl chloride formation reactions, but also be readily removed from the final products without detriment to the appended tetracycline nucleus. The inclusion of protecting groups in this process incurs additional steps and is operationally complex. By the method shown in Scheme II, for every new structural entity, e.g. 9-[(substituted glycyl)amido]-7-(substituted)-6-demethyl-6-deoxytetracycline, a minimum of 4 synthetic steps and as many as 8 synthetic steps would be required.

In contrast, the novel method of the present invention allows the formation of the final product in only two synthetic steps. According to the novel method in Scheme III, the incorporation of the monosubstituted($C_1$-$C_6$)amines or disubstituted($C_1$-$C_6$)amines onto the 9-[(haloacyl)amino]-7-(substituted)-6-demethyl-6-deoxytetracyclines does not require the use of nitrogen protecting groups. Thus, this process allows use of structurally unique or chemically sensitive amines, e.g. amines which may decompose due to excessive acid.

These precious amines could be utilized in the process with operational efficiency. Since many amines are volatile, their removal from the reaction mixture by vacuum distillation will minimize byproducts that can complicate the purification process. By inference, the amines could also be recovered for further use. Most important, a broader diversity of structural entities may be obtained with no more than 2 synthetic steps.

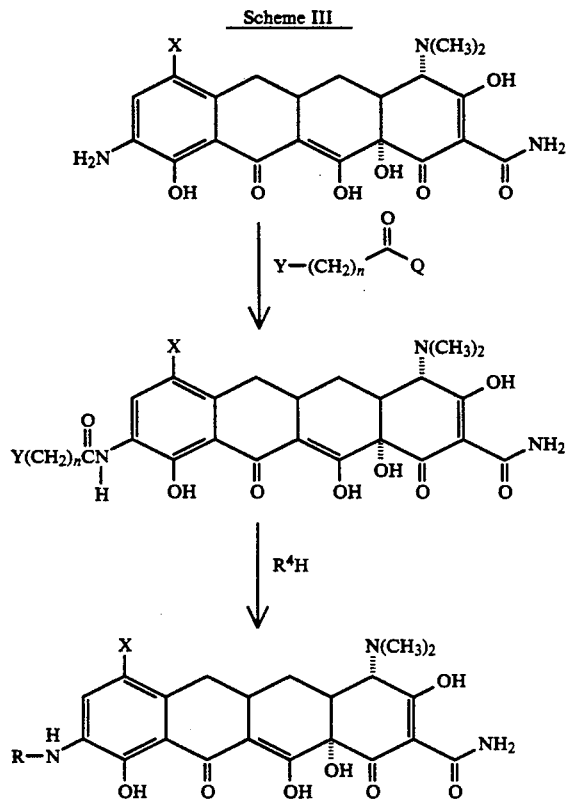

In accordance with the novel method of the present invention, Scheme III, the starting 9-amino-7-(substituted)-6-demethyl-6-deoxytetracycline or the pharmacologically acceptable organic and inorganic salt, prepared by the procedure described in U.S. patent application Ser. No. 771,576, filed Oct. 4, 1991, is mixed with a) a polar-aprotic solvent such as 1,3-dimethyl-3,4,5,6-tetrahydro-2(1H)-pyrimidone hereinafter called DMPU, hexamethylphosphoramide hereinafter called HMPA, 1,3-dimethyl-2-imidazolidinone, dimethylformamide, dimethylacetamide, N-methylpyrrolidone, 1,2-dimethoxyethane or equivalent thereof;

b) an inert solvent, such as acetonitrile, methylene chloride, tetrahydrofuran, chloroform, carbon tetrachloride, 1,2-dichloroethane, tetrachloroethane, diethyl ether, t-butyl methyl ether, isopropyl ether or equivalent thereof:

c) a base such as sodium carbonate, sodium bicarbonate, sodium acetate, potassium carbonate, potassium bicarbonate, triethylamine, cesium carbonate, lithium carbonate or bicarbonate equivalents; and d) a straight or branched haloacyl halide of the formula:

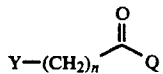

wherein Y, n and Q are as hereinabove defined; such as bromoacetyl bromide, chloroacetyl chloride or 2-bromopropionyl bromide; the halo and halogen in the haloacyl halide can be the same or different and are selected from chlorine, bromine, iodine and fluorine;

e) for 0.5 to 5 hours at from room temperature to the reflux temperature of the reaction; to form the corresponding 9-[(haloacyl)amido]-7-(substituted)-6-demethyl-6-deoxytetracycline or their pharmacologically acceptable organic and inorganic salt.

To produce the 7-(substituted)-9-[(substituted glycyl)amido]-6-demethyl-6-deoxytetracycline or its pharmacologically acceptable organic and inorganic salts, 9-[(haloacyl)amido]-7-(substituted)-6-demethyl-6-deoxytetracycline or their pharmacologically acceptable organic and inorganic salts, is treated, under an atmosphere of argon, nitrogen or helium, with a) a nucleophile R⁴H, wherein R₄ is as defined hereinabove, such as an amine or substituted amine for example methylamine, dimethylamine, ethylamine, n-butylamine, propylamine or n-hexylamine;

b) in a polar-aprotic solvent such as DMPU, HMPA, dimethylformamide, dimethylacetamide, N-methylpyrrolidone, 1,2-dimethoxyethane, tetrahydrofuran, or a polar-protic solvent such as water, methanol or equivalents thereof;

c) for from 0.5-2 hours at room temperature or under reflux temperature to produce the desired 7-(substituted)-9-[(substituted glycyl)amido]-6-demethyl-6-deoxytetracycline, or their pharmacologically acceptable organic and inorganic salts.

In the event that inorganic and organic salt forms are desired, the 7-(substituted)-9-[(substituted glycyl)amido]-6-demethyl-6-deoxytetracyclines, may be obtained as inorganic and organic salts using methods known to those skilled in the art (Richard C. Larock, Comprehensive Organic Transformations, VCH Publishers, 411-415, 1989). It is well known to one skilled in the art that an appropriate salt form is chosen based on physical and chemical stability, flowability, hygroscopicity and solubility. Preferably, the 7-(substituted)-9-[(substituted glycyl)amido]-6-demethyl- 6-deoxytetracyclines are obtained as inorganic salt such as hydrochloric, hydrobromic, hydroiodic, phosphoric, nitric or sulfate; or organic salt such as acetate, benzoate, citrate, cysteine or other amino acids, fumarate, glycolate, maleate, succinate, tartrate, alkylsulfonate or arylsulfonate. Depending on the stochiometry of the acids used, the salt formation occurs with the C(4)-dimethylamino group (1 equivalent of acid) or with both the C(4)-dimethylamino group and the substituent at the R⁴ group (2 equivalents of acid). The salts are preferred for oral and parenteral administration.

Some of the compounds of the hereinbefore described Scheme III have centers of asymmetry at the carbon bearing the R⁴ substituent. The compounds may, therefore, exist in at least two (2) stereoisomeric forms. The present invention encompasses a method of producing the racemic mixture of stereoisomers as well as all stereoisomers of the compounds whether free from other stereoisomers or admixed with stereoisomers in any proportion of enantiomers. The absolute configuration of any compound may be determined by conventional X-ray crystallography. The stereochemistry os the centers on the tetracycline unit (i.e. C-4, C-4a, C-5a and C-12a) remain intact throughout the reaction sequences.

This invention will be described in greater detail with the following non limiting examples.

EXAMPLE 1

(Succinyloxycarbonyl)methyl carbamic acid tert-butyl ester

To a 5° C. solution of 8.76 g of N-(tertbutoxycarbonyl)glycine and 5.75 g of N-hydroxysuccinimide in 100 ml of dioxane and 160 ml of 1,2-dimethoxyethane is added 10.3 g of dicyclohexylcarbodiimide. The mixture is kept at 0° C. for 24 hours. The reaction mixture is filtered, washed with dioxane and the filtrate concentrated in vacuo until a solid results. The solid is triturated with diethyl ether, collected and dried to give 12 g of the desired intermediate.

The above experimental is a literature procedure found in JACS, Vol 86, 1839(1939).

EXAMPLE 2

[7S-(7α,10aα)]-2-[[[9-(Aminocarbonyl)-4,7-bis(dimethylamino)-5,5a,6,6a,7,10,10a12-octahydro-1,8,10a,11-tetrahydroxy-10,12-dioxo-2-naphthacenyl]amino]-2-oxoethyl]carbamic acid 1,1-dimethylethyl ester A mixture of 0.850 g of 9-amino-4,7-bis(dimethylamino)-6-demethyl-6-deoxytetracycline, 0.680 g sodium acetate in 25 ml of tetrahydrofuran and 5 ml of water is stirred at 25° C. for 5 minutes. The solution is treated with 0.359 g of product from Example 1, stirred for 2 hours and extracted with chloroform. The organic layer is concentrated in vacuo to give 0.50 g of the desired product.

MS(FAB): m/z 630 (M+H).

EXAMPLE 3

[4S-(4α,12aα)]-9-[(Aminoacetyl)amino]-4,7-bis(dimethylamino)-1,4,4a,5,5a,6,11,12a-octahydro-3,10,12,12a-tetrahydroxy-1,11-dioxo-2-naphthacenecarboxamide mono(trifluoroacetate)

A solution of 0.030 g of product from Example 2 and 1.0 ml of trifluoroacetic acid is maintained at room temperature for 24 hours followed by concentrating in vacuo. The residue is triturated with methyl alcohol and the solid collected to give 0.024 g of the desired product.

MS(FAB): m/z 530 (M+H).

EXAMPLE 4

Dimethylaminoacetyl chloride hydrochloride

A mixture of 15 g of N,N-dimethylglycine hydrochloride (pulverized and dried in a vacuum oven at 45°-50° C. for 24 hours) and 13.85 ml of thionyl chloride is heated, very slowly, in a sand bath to 78° C. and kept at this temperature for 1½ hours. Toluene is added to the mixture and the excess liquid is removed by pipette. This step is repeated several times. The solid is then transferred to a Buchner funnel, washed with methylene chloride and dried under vacuum at 50° C. for 24 hours to yield 14.2 g of the desired intermediate.

EXAMPLE 5

[4S-(4α,12aα)]-4,7-Bis(dimethylamino)-9-[[(dimethylamino)acetyl]amino]-1,4,4a,5,5a,6,11,12a-octahydro-3, 10,12,12a-tetrahydroxy-1,11-dioxo-2-naphthacenecarboxamide dihydrochloride To a mixture of 6.68 g of 9-amino-4,7-bis(dimethylamino)-6-demethyl-6-deoxytetracycline disulfate in 120 ml of DMPU and acetonitrile is added 6.57 g of sodium carbonate. The mixture is stirred for 5 minutes, followed by the addition of 2.83 g of product from Example 4. The reaction is stirred for 1 hour, filtered and the filtrate is added slowly to a mixture of methylene chloride/ diethyl ether (1200ml/400ml). The solid is collected, dissolved in 250 ml methyl alcohol and added slowly to 1600 ml of methylene chloride. The precipitate is collected, washed with diethyl ether and dried to give 5.75 g of the desired product.

MS(FAB): m/z 558 (M+H).

EXAMPLE 6

[4S-(4α,12aα)]-9-[(Chloroacetyl)amino]-4,7-bis(dimethylamino)-1,4,4a,5,5a,6,11,12a-octahydro-3, 10,12,12a-tetrahydroxy-1,11-dioxo-2-naphthacenecarboxamide dihydrochloride To a room temperature solution of 0.334 g of 9-amino-4,7-bis(dimethyamino)-6-demethyl-6-deoxytetracycline disulfate, 6 ml of 1,3-dimethyl-3,4,5,6-tetrahydro-2(1H)-pyrimidinone, hereinafter called DMPU, and 2 ml of acetonitrile is added 0.318 g of sodium carbonate. The mixture is stirred for 5 minutes followed by the addition of 0.068 g of chloroacetyl chloride. The reaction is stirred for 30 minutes, filtered, and the filtrate added drowise to 100 ml of diethyl ether, containing 1 ml of 1M hydrochloric acid in diethyl ether. The resulting solid is collected and dried to give 0.340 g of the desired intermediate.

MS(FAB): m/z 549 (M+H).

EXAMPLE 6A

[4S-(4α,12aα)]-9-[(Chloroacetyl)amino]-4,7-bis(dimethylamino)-1,4,4a,5,5a,6,11,12a-octahydro-3, 10,12,12a-tetrahydroxy-1,11-dioxo-2-naphthacenecarboxamide (free base)

The title compound is prepared by the procedure of Example 6, using 0.51 g of 9-amino-4,7-bis(dimethylamino)-6-demethyl-6-deoxytetracycline hydrochloride, 50 ml of DMPU, 5 ml of acetonitrile, 0.668 g of sodium carbonate and 0.452 g of chloroacetyl chloride to give 0.52 g of the desired product as the free base.

$^1$H NMR(DMSO-d$_6$): δ9.3(s,1H); 7.9(s,1H); 4.45(s,2H).

EXAMPLE 7

[4S-(4α,12aα)]-9-[(Bromoacetyl)amino]-4,7-bis(dimethylamino)-1,4,4a,5,5a,6,11,12a-octahydro-3,10,12,12a-tetrahydroxy-1,11-dioxo-2-naphthacenecarboxamide monohydrobromide To a solution of 5.01 g of 9-amino-4,7-bis(dimethylamino)-6-demethyl-6-deoxytetracycline disulfate, 100 ml of DMPU and 25 ml of acetonitrile is added 5.0 g of sodium carbonate. The reaction is stirred, under argon, at room temperature for 5 minutes, followed by the addition of 3.03 g of bromoacetyl bromide. The stirring is continued for an additional hour. The solid is collected and the filtrate is added slowly to isopropyl alcohol/diethyl ether (200 ml/750ml). The yellow solid is collected, washed with isopropanol and diethyl ether to give 5.77 g of the desired intermediate.

MS(FAB): 593 (M+H).

EXAMPLE 7A

[4S-(4α,12a)]-9-[(Bromoacetyl)amino]-4,7-bis(dimethylamino)-1,4,4a,5,5a,6,11,12a-octahydro-3, 10,12,12a-tetrahydroxy-1,11-dioxo-2-naphthacenecarboxamide (free base)

To 0.20 g of product from Example 7 in 3 ml of 1,3-dimethyl-2-imidazolidinone is added 0.30 g of sodium bicarbonate. The reaction is stirred at room temperature for 15 minutes and filtered. The filtrate is added to 15 ml of diethyl ether and the resulting precipitate is collected to give 0.150 g of the desired intermediate as the free base.

MS(FAB): m/z 593 (M+H).

EXAMPLE 8

[4S-(4α,12aα)]-9-[(Bromoacetyl)amino]-4,7-bis(dimethylamino)-1,4,4a,5,5a,6,11,12a-octahydro-3, 10,12,12a-tetrahydroxy-1,11-dioxo-2-naphthacenecarboxamide dihydrochloride The title compound is prepared by the procedure of Example 6, using 0.668 g of 9-amino-4,7-bis(dimethylamino)-6-demethyl-6-deoxytetracycline disulfate, 6 ml of DMPU, 2 ml of acetonitrile, 0.636 g of sodium carbonate and o.215 g of bromoacetyl chloride. Seven tenths of a gram of the desired intermediate is obtained.

MS(FAB): m/z 593 (M+H).

EXAMPLE 9

[4S-(4α,12aα)]-9-[(2-Bromo-1-oxopropyl)amino]-4,7-bis(dimethylamino)-1,4,4a,5,5a,6,11,12a-octahydro-3,10,12,12a-tetrahydroxy-1,11-dioxo-2-naphthacenecarboxamide hydrobromide The title compound is prepared by the procedure of Example 6, using 1.00 g of 9-amino-4,7-bis bis(dimethylamino)-6-demethyl-6-deoxytetracycline disulfate, 1.0 g of sodium carbonate and 0.648 g of 2-bromopropionyl bromide to give 0.981 g of the desired intermediate.

MS(FAB): m/z 607 (M+H).

EXAMPLE 10

[4S-(4α,12aα)]-9-[(4-Bromo-1-oxobutyl)amino]-4,7-bis(-dimethylamino)-1,4,4a,5,5a,6,11,12a-octahydro-3,10,12,12a-tetrahydroxy-1,11-dioxo-2-naphthacenecarboxamide dihydrochloride The title compound is prepared by the procedure of Example 6, using 1.34 g of 9-amino-4,7-bis(dimethylamino)-6-demethyl-6-deoxytetracycline disulfate, 1.3 g of sodium carbonate, 24 ml of DMPU, 8 ml of acetonitrile and 0.389 g of 4-bromobutyryl chloride to give 1.45 g of the desired product.

EXAMPLE 11

[4S-(4α,12aα)]-4,7-Bis(dimethylamino)-9-[[(dimethylamino)acetyl]amino]-1,4,4a,5,5a,6,11,12a-octahydro-3, 10,12,12a-tetrahydroxy-1,11-dioxo-2-naphthacenecarboxamide dihydrochloride To a solution of 0.15 g of product from Example 6 in 4 ml of DMPU is added 0.85 g of dimethylamine (40% in water). The reaction is stirred for 20 minutes followed by concentration in vacuo to remove excess dimethylamine. The mixture is filtered and the filtrate added, dropwise, to 70 ml of isopropyl alcohol/diethyl ether (1:1). To this solution is added 1 ml of 1M hydrochloric acid/diethyl ether. The resulting precipitate is collected, washed with 0.11 g of the desired product.

MS(FAB): m/z 558 (M+H).

EXAMPLE 12

[4S-(4α,12aα)]-4,7-Bis(dimethylamino)-1,4,4a,5-,5a,6,11,12a-octahydro-3,10,12,12a-tetrahydroxy-9-[[(methylamino)acetyl]amino]-1,11-dioxo-2-naphthacenecarboxamide dihydrochloride A mixture of 0.1258 g of product from Example 7, 5 ml of 40% methylamine in water and 5 ml of methyl alcohol, under Argon, is stirred at room temperature for 30 minutes. The excess methylamine is removed in vacuo and the residue diluted with a small volume of methyl alcohol. The diluted reaction solution is added dropwise to 100 ml of diethyl ether containing 1 ml of 1M hydrochloric acid in diethyl ether and 10 ml of isopropyl alcohol. The resulting solid is collected and dried to give 0.106 g of the desired product.

MS(FAB): m/z 544 (M+H).

Substantially following the methods described in detail herein above in Example 12, the compounds of this invention listed below in Examples 13–33 are prepared.

| Example # | Name | Starting Material Prod. of Exp. | Reactant | Rx Time | MS (FAB): m/z |
|---|---|---|---|---|---|
| 13 | [7S-(7alpha,10aalpha)]-N-[9-(Aminocarbonyl)-4,7-bis(dimethylamino)-5,5a,6,6a,7,10,10a,12-octahydro-1,8,-10a,11-tetrahydroxy-10,12-dioxo-2-naphthacenyl]-4-morpholineacetamide dihydrochloride | 7 | Morpholine | 0.5 hr. | 600 (M + H) |
| 14 | [4S-(4alpha,12aalpha)[-4,7-Bis(dimethylamino)-9-[(ethylamino)acetyl]amino]-1,4,4a,5,5a,6,11,12a-octahydro-3,10,-12,12a-tetrahydroxy-1,11-dioxo-2-naphthacenecarboxamide dihydrochloride | 7 | Ethylamine (70% in water) | 2 hr. | 558 (M + H) |
| 15 | [4S-(4alpha,12aalpha)]-9-[[(Cyclopropylamino)acetyl]amino]-4,7-bis(dimethylamino)-1,4,4a,5,5a,6,11,12a-octahydro-3,10,12,12a-tetrahydroxy-1,11-dioxo-2-naphthacenecarboxamide dihydrochloride | 7 | Cyclopropylamine | 2 hr. | 570 (M + H) |
| 16 | [4S-(4alpha,12aalpha)]-4,7-Bis(dimethylamino)-9-[[(butylamino)acetyl]amino]-1,4,4a,5,5a,6,11,12a-octahydro-3,10,12,12a-tetrahydroxy-1,11-dioxo-2-naphthacenecarboxamide dihydrochloride | 7 | Butylamine | 2 hr. | 586 (M + H) |
| 17 | [4S-(4alpha,12aalpha)]-9-[[(Diethylamino)acetyl]amino]-4,7-bis(dimethylamino)-1,4,4a-5,5a,6,11,12a-octahydro-3,10,12,12a-tetrahydroxy-1,11-dioxo-2-naphthacenecarboxamide dihydrochloride | 7 | Diethylamine | 2 hr. | 586 (M + H) |
| 18 | [7S-(7alpha,10aalpha)]-N-]9-(Aminocarbonyl)-4,7-bis(dimethylamino)-5,5a,6,6a,7,10a,12-octahydro-1,8,10a,11-tetrahydroxy-10,12-dioxo-2-naphthacenyl]-1-pyrrolidineacetamide dihydrochloride | 7 | Pyrrolidine | 0.5 hr. | 584 (M + H) |
| 19 | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-1-piperidineacetamide dihydrochloride | 7 | Piperidine | 1 hr. | 598 (M + H) |
| 20 | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-1-azetidineacetamide | 7 | Azetidine | 0.5 hr. | 570 (M + H) |
| 21 | [4S-(4alpha,12aalpha)]-4,7-Bis(dimethylamino)-1,4,4a,5,5a,6,11,12a-octahydro-3,10,12,12a-tetrahydroxy-1,11-dioxo-9-[[(propylamino)acetyl]amino]-2-naphthacenecarboxamide dihydrochloride | 7 | Propylamine | 0.75 hr. | 572 (M + H) |
| 22 | [4S-(4alpha,12aalpha)]-4,7-Bis(dimethylamino)-9-[[(hexylamino)acetyl]amino]-1,4,4a,5,5a,6,11,12a-octahydro-3,10,12,-12a-tetrahydroxy-1,11-dioxo-2-naphthacenecarboxamide dihydrochloride | 7 | N-Hexylamine | 2 hr. | 614 (M + H) |
| 23 | [4S-(4alpha,12aalpha)]-4,7-Bis(dimethylamino)-9-[[2-(dimethylamino)-1-oxopropyl]amino]-1,4,4a,5,5a,6,aa,12a-octahydro-3,10,12,12a-tetrahydroxy-1,11-dioxo-2-naphthacenecarboxamide dihydrochloride | 9 | Dimethylamine (40% in water) | 2.5 hr. | 572 (M + H) |
| 24 | [4S-(4alpha,12aalpha)]-4,7-Bis(dimethyl- | 9 | Methylamine | 2 hr. | 558 (M + H) |

-continued

| Example # | Name | Starting Material Prod. of Exp. | Reactant | Rx Time | MS (FAB): m/z |
|---|---|---|---|---|---|
|  | amino)-1,4,4a,5,5a,6,11,12a-octahydro-3,10,12,12a-tetrahydroxy-9-[[2-(methyl-amino)-1-oxopropyl]amino]-1,11-dioxo-2-naphthacenecarboxamide dihydrochloride |  | (40% in water) |  |  |
| 25 | [7S-(7alpha,10aalpha)]-N-[9-(Aminocar-bonyl)-4,7-bis(dimethylamino)-5,5a,6,6a-7,10,10a,12-octahyhdro-1,8,10a,11-tetra-hydroxy-10,12-dioxo-2-naphthacenyl]-alpha-methyl-1-pyrrolidineacetamide dihydrochloride | 9 | Pyrrolidine | 1 hr. | 598 (M + H) |
| 26 | [4S-(4alpha,12aalpha)]-4,7-bis(dimethyl-amino)-1,4,4a,5,5a,6,11,12a-octahydro-3,10,12,12a-tetrahydroxy-1,11-dioxo-9-[[(pentylamino)acetyl]amino]-2-naphthacenecarboxamide dihydrochloride | 7 | Amylamine | 2 hr. | 600 (M + H) |
| 27 | [4S-(4alpha,12aalpha)]-4,7-Bis(di-methylamino)-1,4,4a,5,5a,6,11,12a-octahydro-3,10,12,12a-tetrahydroxy-9-[[[(2-methylpropyl)amino]acetyl]-amino]-1,11-dioxo-2-naphthacenecar-boxamide dihydrochloride | 7 | Isobutylamine | 2 hr. | 586 (M + H) |
| 28 | [7S-(7alpha,10aalpha)]-N-[9-(Amino-carbonyl)-4,7-bis(dimethylamino)-5,5a,6,6a,7,10,10a,12-octahydro-1,8,10a,11-tetrahydroxy-10,12-dioxo-2-naphthacenyl]-1H-imidazole-1-acetamide dihydrochloride | 7 | Imidazole | 1 hr. | 581 (M + H) |
| 29 | [4S-(4alpha,12aalpha)]-4,7-bis(di-methylamino)-9-[[(dimethylamino)-acetyl]amino]-1,4,4a,5,5a,6,11,12a-octahydro-3,10,12a-tetrahydroxy-1,11-dioxo-2-naphthacenecarboxamide disulfate | 7 | Dimethylamine | 0.5 hr. | 558 (M + H) |
| 30 | [4S-(4alpha,12aalpha,)]-4,7-bis(di-methylamino)-9-[[(dimethylamino)-acetyl]amino]-1,4,4a,5,5a,6,11,12a-octahydro-3,10,12,12a-tetrahydroxy-1,11-dioxo-2-naphthacenecarboxamide | 7 | Dimethylamine | 0.5 hr. | 558 (M + H) |
| 31 | [4S-(4alpha,12aalpha)]-4,7-Bis(di-methylamino)-9-[[4-(dimethylamino)-1-oxobutyl]amino]-1,4,4a,5,5a,6,11,12a-octahydro-3,10,12,12a-tetrahydroxy-1,11-dioxo-2-naphthacenecarboxamide dihydro-chloride | 10 | Dimethylamine (40% in water) | 2 hr. | 586 (M + H) |
| 32 | [4S-(4alpha,12aalpha)]-9-[[(Butylmethyl-amino)acetyl]amino]-4,7-bis(dimethyl-amino)-1,4,4a,5,5a,6,11,12a-octahydro-3,10,12,12a-tetrahydroxy-1,11-dioxo-2-naphthacenecarboxamide dihydrochloride | 7 | N-Methylbutyl-amine | 2 hr. | 600 (M + H) |
| 33 | [4S-(4alpha,12aalpha)]-4,7-bis(dimethyl-amino)-1,4,4a,5,5a,6,11,12a-octahydro-3,10,12,12a-tetrahydroxy-1,11-dioxo-9-[[[(phenylmethyl)amino]acetyl]amino]-2-naphthacenecarboxamide dihydrochloride | 7 | Benzylamine | 1 hr. | 620 (M + H) |

EXAMPLE 34

[7S-(7α,10aα)]-N-[2-[[9-(Aminocarbonyl)-4,7-bis(dime-thylamino)-5,5a,6,7,10a,12-octahydro-1,8,10a,11-tet-rahydroxy-10,12-dioxo-2-naphthacenyl]amino]-2-oxoe-thyl]glycine phenylmethyl ester To 0.30 g of benzylglycine hydrochloride in 3 ml of 1,3-dimethyl-2-imidazolidinone is added 0.60 g of sodium bicarbonate. The mixture is stirred at room temperature for 15 minutes and filtered. To the filtrate is added 0.20 g of product from Example 7A. The reaction mixture is stirred at room temperature for 1 hour and then added to diethy ether. The resulting solid is collected.

EXAMPLE 43

[7S-(7α,10aα)]-N-[2-[[9-(Aminocarbonyl)-4,7-bis(dimethylamino)-5,5a,6,7,10a,12-octahydro-1,8,10a,11-tetrahydroxy-10,12-dioxo-2-naphthacenyl]amino]-2-oxoethyl]glycine One-tenth of a gram of product from Example 34 in 10 ml of 2-methoxyethane is reduced catalytically, in a Parr shaker, with 0.10 g of 10% palladium on carbon, at 30 psi of hydrogen, for 2 hours. The reaction mixture is filtered and the filtrate concentrated to give 0.050 g of the desired product. FAB-MS: m/z 588 (M+H).

We claim:

1. A process for producing 7-(substituted)-9-[(substituted glycyl)amido]-6-demethyl-6-deoxytetracyclines of the formula:

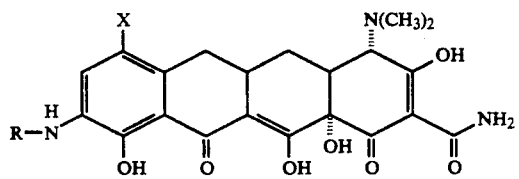

wherein:
X is selected from amino, —NR¹R², or halogen; the halogen is selected from bromine, chlorine, fluorine or iodine; R¹ is selected from hydrogen, methyl, ethyl, n-propyl, 1,1-dimethylethyl, n-butyl, or 1-methylpropyl and R² is selected from methyl, ethyl, n-propyl, 1-methylethyl, n-butyl, 1methylpropyl, 2-methylpropyl, or 1,1-dimethylethyl with the proviso that when R¹=hydrogen, R²=methyl, ethyl, n-propyl, 1-methylethyl, n-butyl, 1-methylpropyl, 2-methylpropyl or 1,1-dimethylethyl and when R¹=methyl or ethyl, R²=methyl, ethyl, n-propyl, 1-methylethyl, n-butyl, 1-methylpropyl or 2-methylpropyl; and when R¹=n-propyl, R²=n-propyl, 1-methylethyl, n-butyl, 1-methylpropyl or 2-methylpropyl; and when R¹=1-methylethyl, R²=n-butyl, 1-methylpropyl or 2-methylpropyl; and when R¹=n-butyl, R²=n-butyl, 1-methylpropyl or 2-methylpropyl; and when R¹=1-methylpropyl, R²=2-methylpropyl;

R is selected from R⁴(CH₂)ₙCO, n=0–4, R⁴ is an α-amino(C₁–C₄)alkyl group selected from α-aminomethyl, α-aminoethyl, α-aminopropyl, α-aminobutyl or the enantiomers of said α-amino(C₁–C₄)alkyl group; an α-aralkylamino group selected from phenylglycyl or the enantiomers of said α-aralkylamino group; an amino group; a monosubstituted amino group with substitution selected from methyl, ethyl, n-propyl, 1-methylethyl, n-butyl, 1-methylpropyl, 2-methylpropyl, 1,1-dimethylethyl, n-pentyl, 2-methylbutyl, n-pentyl, 2-methylbutyl, 1,1-dimethylpropyl, 2,2-dimethylpropyl, 2,2-dimethylbutyl, 3-methylpentyl, 1,2-dimethylbutyl, 1,3-dimethybutyl, 1-methyl-2-ethylpropyl, cyclopropyl, cyclobutyl, benzyl or phenyl; a disubstituted amino group selected from dimethylamino, diethylamino, methyl(butyl)amino, ethyl(1-methylethyl)amino, monomethylbenzylamino; or a carboxy (C₂–C₄)alkylamino group selected from aminoacetic acid, α-aminopropionic acid or the enantiomers of said carboxy (C₂–C₄)alkylamino-group; with the proviso that and when n=0, R⁴ is an α-amino(C₁–C₄)alkyl group selected from α-aminomethyl, α-aminoethyl, α-aminopropyl, α-aminobutyl or the enantiomers of said α-amino(C₁–C₄)alkyl group; an α-aralkylamino group selected from phenylglycyl or the enantiomers of said α-aralkylamino group; and when n=1–4, R⁴ is an amino group; a monosubstituted amino group with substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethybutyl 1-methyl-2-ethylpropyl, cyclopropyl, cyclobutyl, benzyl or phenyl; a disubstituted amino group selected from dimethylamino, diethylamino, methyl(butyl)amino, ethyl(1-methylethyl)amino, monomethylbenzylamino; or a carboxy(C₂–C₄)alkylamino group selected from aminoacetic acid, α-aminopropionic acid or the enantiomers of said carboxy(C₂–C₄)alkylamino group; which comprises (a) mixing 9-amino-7-(substituted)-6-demethyl-6-deoxytetracycline or the pharmacologically acceptable salts thereof with a polar-aprotic solvent, an inert solvent, and a base and reacting with a straight or branched haloacyl halide of the formula:

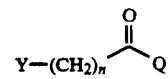

wherein:
Q is a halogen selected from bromine, chlorine, fluorine or iodine; and n=0 to 4; and when n=0, Y is a straight or branched α-halo (C₁–C₄)alkyl group selected from bromomethyl, chloromethyl, iodomethyl, α-bromoethyl, α-chloroethyl, α-bromobutyl or α-chloro-isobutyl; and when n=1,4, Y is halogen selected from bromine, chlorine, iodine or fluorine; an O-toluenesulfonate, O-methylsulfonate or trifluoromethylsulfonate; for 0.5 to 5 hours at from room temperature to the reflux temperature of the reaction and recovering 9-[(haloacyl)amido]-7-(substituted)-6-demethyl-6-deoxyltetracycline or the pharmacologically acceptable salts thereof; and (b) reacting the 9-[(haloacyl)amido]-7-(substituted)-6-demethyl-6-deoxytetracycline or the pharmacologically acceptable salts thereof, in a polar-aprotic solvent, under an inert atmosphere of helium, nitrogen or argon, with a nucleophile having the formula, R⁴H, wherein R⁴ is hereinabove defined; for from 0.5 to 2 hours at from room temperature to the reflux temperature of the reaction and isolating the compound of formula I or the pharmacologically acceptable salts thereof.

2. The process of claim 1 wherein: R¹ is selected from hydrogen, methyl or ethyl and R² is selected from methyl, ethyl, n-propyl, 1-methylethyl, n-butyl, 1-methylpropyl 2-methylpropyl or 1,1-dimethylethyl with the proviso that when R¹-hydrogen, R²=methyl, ethyl, n-propyl, 1-methylethyl, n-butyl, 1-methylpropyl, 2-methylpropyl or 1,1-dimethylethyl; and when R¹=methyl or ethyl, R²=methyl, ethyl, n-propyl, 1-methylethyl, or n-butyl.

3. The process of claim 1 wherein: n=0,
R⁴ is an α-amino(C₁–C₄)alkyl group selected from α-aminomethyl, α-aminoethyl, α-aminopropyl, α-aminobutyl, or the enantiomers of said α-amino(C₁–C₄)alkyl group; and when n=1–4,
R⁴ is aminoacetic acid.

4. The process of claim 1 wherein: X is selected from amino, —NR¹R², or halogen, the halogen is selected from bromine, chlorine, fluorine or iodine; $R^1$ and $R^2$ are selected from methyl or ethyl, when $n=0$, $R^4$ is an α-amino($C_1$-$C_4$)alkyl group selected from α-aminomethyl, α-aminoethyl, or the enantiomers of said α-amino($C_1$-$C_4$)alkyl group; and when $n=1,4$, $R^4$ is amino; a monosubstituted amino group with substitution selected from methyl, ethyl, n-propyl, 1-methylethyl, n-butyl, n-pentyl, n-hexyl, cyclopropyl or benzyl; a disubstituted amino group selected from dimethylamino, diethylamino, or methyl(butyl)amino.

5. The process of claim 1 wherein said polar-aprotic solvent is selected from 1,3-dimethyl-3,4,5,6-tetrahydro-2(1H)pyrimidone, 1,3-dimethyl-2-imidazolidinone, hexamethylphosphoramide, dimethylformamide, dimethylacetamide, N-methylpyrrolidone, 1,2-dimethyoxyethane, tetrahydrofuran, water, or methanol.

6. The process of claim 1 wherein said inert solvent is selected from acetonitrile, methylene chloride, tetrahydrofuran, chloroform, carbon tetrachloride, 1,2-dichloroethane, tetrachloroethane, diethyl either, t-butyl methyl ether, or isopropyl ether.

7. The process of claim 1 wherein said base is selected from sodium carbonate, sodium bicarbonate, sodium acetate, potassium carbonate, potassium bicarbonate, triethylamine, cesium carbonate, or lithium carbonate.

8. A process of producing novel straight or branched 9-[(haloacyl)amido]-7-(substituted)-6-demethyl-6-deoxytetracylclines of the formula:

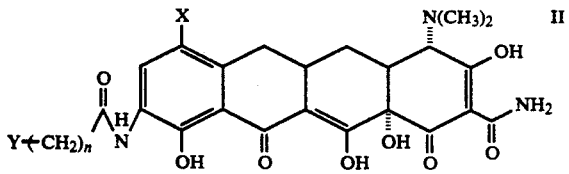

wherein:

X is selected from amino, —$NR^1R^2$, or halogen; the halogen is selected from bromine, chlorine, fluorine or iodine; $R^1$ is selected from hydrogen, methyl, ethyl, n-propyl, 1,1-dimethylethyl, n-butyl, or 1-methylpropyl and $R^2$ is selected from methyl, ethyl, n-propyl, 1-methylethyl, n-butyl, 1methylpropyl, 2-methylpropyl, or 1,1-dimethylethyl with the proviso that when $R^1$=hydrogen, $R^2$=methyl, ethyl, n-propyl, 1-methylethyl, n-butyl, 1-methylpropyl, 2-methylpropyl or 1,1-dimethylethyl; and when $R^1$=methyl or ethyl, $R^2$=methyl, ethyl, n-propyl, 1-methylethyl, n-butyl, 1-methylpropyl or 2-methylpropyl; and when $R^1$=n-propyl, $R^2$=n-propyl, 1-methylethyl, n-butyl, 1-methylpropyl or 2-methylpropyl; and when $R^1$=1-methylethyl, $R^2$=n-butyl, 1-methylpropyl or 2-methylpropyl; and when $R^1$=n-butyl, $R^2$=n-butyl, 1-methylpropyl or 2-methylpropyl; and when $R^1$=1-methylpropyl, $R^2$=2-methylpropyl; $n=0-4$; when $n=0$, Y is a straight or branched α-halo ($C_1$-$C_4$)alkyl group selected from bromomethyl, chloromethyl, iodomethyl, α-bromoethyl, α-chloroethyl, α-bromobutyl or α-chloro-isobutyl; and when $n=1-4$, Y is halogen selected from bromine, chlorine, iodine or fluorine; an O-toluenesulfonate, O-methylsulfonate or trifluoromethylsulfonate; which comprises (a) mixing 9-amino-7-(substituted)-6-demethyl-6-deoxytetracycline or the pharmacologically acceptable salts thereof with a polar-aprotic solvent, an inert solvent, and a base and reacting with a straight or branched haloacyl halide of the formula:

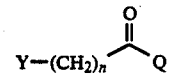

wherein Y and n are hereinabove defined and Q is a halogen selected from bromine, chlorine, fluorine or iodine; for 0.5 to 5 hours at from room temperature to the reflux temperature of the reaction and isolating the compound of formula II or the pharmacologically acceptable salts thereof.

9. The process of claim 8 wherein: $R^1$ is selected from hydrogen, methyl or ethyl and $R^2$ is selected from methyl, ethyl, n-propyl, 1-methylethyl, n-butyl, 1-methylpropyl 2-methylpropyl or 1,1-dimethylethyl with the proviso that when $R^1$-hydrogen, $R^2$=methyl, ethyl, n-propyl, 1-methylethyl, n-butyl, 1-methylpropyl, 2-methylpropyl or 1,1-dimethylethyl; and when $R^1$=methyl or ethyl, $R^2$=methyl, ethyl, n-propyl, 1-methylethyl, or n-butyl.

10. The process of claim 8 wherein: X is selected from amino, —$NR^1R^2$, or halogen; the halogen is selected from bromine, chlorine, fluorine or iodine; $R^1$ and $R^2$ are selected from methyl or ethyl, when $n=0$, Y is a straight or branched α-halo($C_1$-$C_4$)alkyl group selected from bromomethyl, chloromethyl, iodomethyl, α-bromoethyl, α-chloroethyl, α-bromobutyl or α-chloro-isobutyl; and when $n=1,4$, Y is a halogen selected from bromine, chlorine, iodine or fluorine; an O-toluenesulfonate, O-methylsulfonate or trifluoromethylsulfonate.

11. The process of claim 8 wherein said polar-aprotic solvent is selected from 1,3-dimethyl-3,4,5,6-tetrahydro-2(1H)pyrimidone, 1,3-dimethyl-2-imidazolidinone, hexamethylphosphoramide, dimethylformamide, dimethylacetamide, N-methylpyrrolidone, or 1,2-dimethyoxyethane.

* * * * *